United States Patent [19]

Willis et al.

[11] 4,276,220

[45] Jun. 30, 1981

[54] NOVEL NORBORNYL-SUBSTITUTED PYRANS, METHOD FOR THEIR SYNTHESIS AND USE THEREOF IN PERFUMERY

[75] Inventors: Brian J. Willis, Bergenfield, N.J.; John W. Dittrick, Flushing, N.Y.

[73] Assignee: Fritzsche Dodge & Olcott, Inc., New York, N.Y.

[21] Appl. No.: 123,654

[22] Filed: Feb. 22, 1980

Related U.S. Application Data

[62] Division of Ser. No. 60,589, Jul. 25, 1979, Pat. No. 4,221,679.

[51] Int. Cl.³ .......................................... C07D 309/18
[52] U.S. Cl. ............................................... 260/345.1
[58] Field of Search ................................... 260/345.1

[56] References Cited

U.S. PATENT DOCUMENTS

| | | | |
|---|---|---|---|
| 4,071,535 | 1/1978 | Vinals et al. | 260/345.1 |
| 4,197,246 | 4/1980 | Willis et al. | 260/345.1 |

*Primary Examiner*—Nicky Chan
*Attorney, Agent, or Firm*—Kenyon & Kenyon

[57] ABSTRACT

Norbornyl-substituted pyrans, their preparation and their use as olfactory components of perfume formulations are disclosed.

5 Claims, No Drawings

NOVEL NORBORNYL-SUBSTITUTED PYRANS, METHOD FOR THEIR SYNTHESIS AND USE THEREOF IN PERFUMERY

This is a division of application Ser. No. 60,589 filed July 25, 1979, now U.S. Pat. No. 4,221,679 granted Sept. 9, 1980.

DISCLOSURE

This invention is concerned with certain novel chemicals containing a bicyclo(2.2.1)heptane or bicyclo(2.2.1)heptene moiety and an oxacyclohexane or oxacyclohexene moiety and the use of such chemicals as olfactory constituents of perfume formulations.

More specifically, the present invention is concerned with chemicals which may be represented by the structural formula:

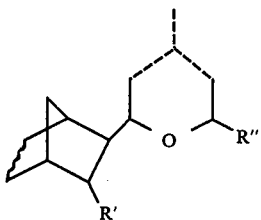

wherein the wavy line represents either a carbon-carbon single bond or a carbon-carbon double bond, the dashed lines represent either a carbon-carbon single bond or a carbon-carbon double bond, such that two of the three dashed lines represent a single bond, and R' and R" are hydrogen or methyl.

The bicyclo(2.2.1)heptane moiety also may be classified as the "norbornyl" moiety, while the oxacyclohexane and oxacyclohexene moieties may be classified generally as "pyran" moieties. Hence, for convenience the foregoing chemicals will be referred to collectively as "norbornyl-substituted pyrans". The present invention is further concerned with the use of "norbornyl-substituted pyrans" as olfactory components of perfume compositions.

BACKGROUND OF THE INVENTION

Considerable time and effort are expended by research chemists in the search for new and inexpensive chemicals which can be used as flavor and fragrance modifiers or enhancers in various consumable materials. These substances are used to reduce or replace those natural compounds presently employed which are in diminishing or sporadic supply. They also are employed in creating entirely new flavors and fragrances.

Certain chemicals having the pyran ring have been found to be useful for imparting fragrance and/or flavor to compositions of which they are constituents. For example, Japanese application Ser. No. 7,4011-073 published Mar. 14, 1974, discloses 2,5-diethyltetrahydropyran chemicals having a rose-like scent, while 3-hydroxy-2-methyl-1,4-pyran, or maltol, is disclosed in "Perfume and Flavor Chemicals", Arctander Vol. II, No. 1831, as possessing "a warm-fruity, caramellic-sweet odor with emphasis on the caraway note in the dry state."

U.S. Pat. No. 3,901,924, granted Aug. 26, 1975, discloses certain 1,1-dialkylnaphthopyrans, as well as certain chypre and fougere type perfume formulations of which these pyrans are constituents. Examples of these pyrans are the following:

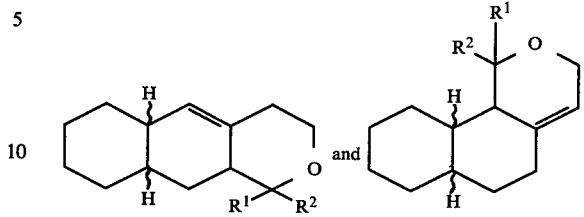

wherein each of $R^1$ and $R^2$ represents a lower alkyl group.

U.S. Pat. No. 4,010,286, granted Mar. 1, 1977, discloses various substituted spiropyrans which exhibit a variety of odors and/or flavors, including those characterized as spicy, dill, green, floral, herbal, eucalyptol-like, woody, fruity, berry-like, sweet, minty and weedy, and which are useful as flavoring and fragrance imparters or modifiers. Examples of the spiropyrans disclosed in this patent are the following:

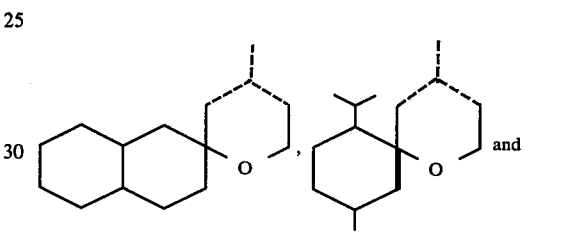

wherein the dashed lines represent carbon-carbon double bonds; and wherein the presence of two dashed lines in a single structure representation indicates a mixture of double bond isomers. Still other spiropyrans which are disclosed are the product of the reaction of dihydro verdyl ketone or verdyl ketone with 3-methyl-3-buten-1-ol, which is represented by the following formula:

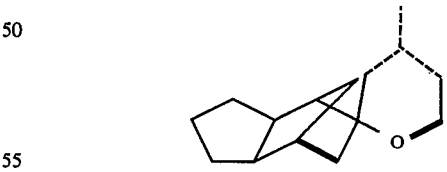

Methods of preparation of other pyran chemicals have also been disclosed in the prior art. For example, U.S. Pat. No. 2,422,648, granted June 17, 1947, discloses a method for the preparation of certain dihydropyran chemicals which comprises reacting a ketone with an unsaturated alcohol containing an unsaturated tertiary carbon atom linked directly by a single bond to a saturated carbon atom which is directly attached to the carbinol carbon atom, in the presence of an acidic condensation catalyst at a temperature of about about 50° C., but not substantially above the temperature of dehydration of the alcohol.

In addition, methods of preparation of both rose oxide and nerol oxide, known odoriferous components of Bulgarian rose oil, are disclosed in Tetrahedron Letters, 51, 4507 (1970) by J. H. P. Tyman and B. J. Willis. These chemicals are prepared from the reaction of 3-methyl-2-butenal with 2-methyl-1-buten-4-ol under acidic conditions.

The chemicals described in each of the above patents and articles are different in kind from the chemicals of the instant invention from a structural standpoint, and from the standpoint of their fragrance properties. The chemicals of the instant invention possess unexpected, unobvious and advantageous properties from the standpoint of quality, character of fragrance when used in fragrance compositions.

The chemicals of this invention also are related to the "norcamphanyl"-substituted pyrans of our co-pending application Ser. No. 950,598 filed Oct. 12, 1978 now U.S. Pat. No. 4,197,246 granted Apr. 8, 1980, and which may be represented by the structural formula.

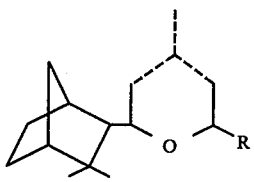

Structurally, the chemicals of this invention differ from those of our prior application in that there is no more than one substituent at the 3-position of the norbornyl nucleus, and there may be a double bond between the 5- and 6-carbons. Furthermore, the chemicals differ materially in their odor characteristics. The chemicals of this invention are characterized by green, woody, sweet, fruity, aldehydic odors, whereas the chemicals of our prior application are characterized by soft, dry woody odors with green pepper notes.

THE INVENTION

In accordance with this invention, there have been discovered novel norbornyl-substituted pyrans, as represented by the above formula, which are useful in perfume formulations for imparting green, woody, sweet, fruity, aldehydic notes to such compositions. It will be recognized that the chemicals of this invention can exist in several stereoisomeric forms, including the "dextro" and "laevo", as well as the "cis", "trans" isomers. The foregoing structural formula is intended to embrace the individual stereoisomers, as well as mixtures of the various stereoisomers of the norbornyl-substituted pyrans of this invention.

According to currently accepted nomenclature, and disregarding stereoisomers, the chemicals within the formula are:

When R' and R" are hydrogen
2-(bicyclo[2.2.1]hept-2-yl)-4-methyloxacyclohex-3-ene;
2-(bicyclo[2.2.1]hept-5-en-2-yl)-4-methyloxacyclohex-3-ene;
2-(bicyclo[2.2.1]hept-2-yl)-4-methyloxacyclohex-4-ene;
2-(bicyclo[2.2.1]hept-5-en-2-yl)-4-methyloxacyclohex-4-ene;
2-(bicyclo[2.2.1]hept-2-yl)-4-methyleneoxacyclohexane; and
2-(bicyclo[2.2.1]hept-5-en-2-yl)-4-methyleneoxacyclohexane.

When R' is hydrogen and R" is methyl
2-(bicyclo[2.2.1]hept-2-yl)-4,6-dimethyloxacyclohex-3-ene;
2-(bicyclo[2.2.1]hept-5-en-2-yl)-4,6-dimethyloxacyclohex-3-ene;
2-(bicyclo[2.2.1]hept-2-yl)-4,6-dimethyloxacyclohex-4-ene;
2-(bicyclo[2.2.1]hept-5-en-2-yl)-4,6-dimethyloxacyclohex-4-ene;
2-(bicyclo[2.2.1]hept-2-yl)-4-methylene-6-methyloxacyclohexane; and
2-(bicyclo[2.2.1]hept-5-en-2-yl)-4-methylene-6-methyloxacyclohexane.

When R' is methyl and R" is hydrogen
2-(2-methylbicyclo[2.2.1]hept-3-yl)-4-methyloxacyclohex-3-ene:
2-(2-methylbicyclo[2.2.1]hept-5-en-3-yl)-4-methyloxacyclohex-3-ene;
2-(2-methylbicyclo[2.2.1]hept-3-yl)-4-methyloxacyclohex-4-ene;
2-(2-methylbicyclo[2.2.1]hept-5-en-3-yl)-4-methyloxacyclohex-4-ene;
2-(2-methylbicyclo[2.2.1]hept-3-yl)-4-methyleneoxacyclohexane; and
2-(2-methylbicyclo[2.2.1]hept-5-en-3-yl)-4-methyleneoxacyclohexane.

When R' and R" are methyl
2-(2-methylbicyclo[2.2.1]hept-3-yl)-4,6-dimethyloxacyclohex-3-ene;
2-(2-methylbicyclo[2.2.1]hept-5-en-3-yl)-4,6-dimethyloxacyclohex-3-ene;
2-(2-methylbicyclo[2.2.1]hept-3-yl)-4,6-dimethyloxacyclohex-4-ene;
2-(2-methylbicyclo[2.2.1]hept-5-en-3-yl)-4,6-dimethyloxacyclohex-4-ene;
2-(2-methylbicyclo[2.2.1]hept-3-yl)-4-methylene-6-methyloxacyclohexane; and
2-(2-methylbicyclo[2.2.1]hept-5-en-3-yl)-4-methylene-6-methyloxacyclohexane.

The novel chemicals of this invention are prepared by reacting the corresponding readily available aldehydes with either 2-methyl-1-penten-4-ol or 2-methyl-1-buten-4-ol in the presence of an acid catalyst. This reaction may be represented by the general equation:

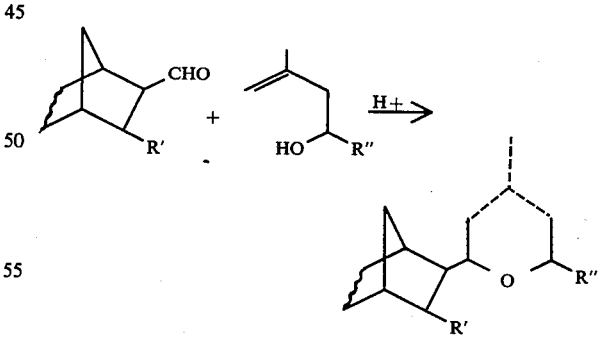

wherein R', R" and the wavy and dashed lines have the meanings set forth above. The proportions of the two reactants are not critical, and either may be employed in molar excess. For reasons of economy, it is preferred to employ the least expensive reactant in excess, generally in a molar ratio of from about 1:1 to about 1.5:1.

Acids which may be employed as a catalyst for these reactions include inorganic acids such as sulfuric acid and perchloric acid, and organic acids such as the sulfonic acids. Cation exchange resins, for example those containing the sulfonic acid moiety(—SO₃H), may be employed.

The reaction conveniently is carried out in an inert organic solvent, preferably an organic hydrocarbon solvent. Such solvents include aromatic solvents such as benzene and toluene, as well as aliphatic solvents such as hexane or heptane. It is desirable to heat the reaction mixture and to remove the water evolved during the reaction in order to maximize the yield of norbornyl-substituted pyrans.

The chemicals of this invention are recovered from the reaction mixture through the use of conventional procedures, for example, the acid is neutralized and the organic products fractionated to yield a mixture of norbornyl-substituted pyran isomers. The mixture may be employed directly, or the isomers may be separated by techniques known to the art.

As used herein, the term "alter" is intended to mean "supply or impart an odorant character or note to an otherwise bland, relatively odorless substance, or augment or enhance the existing odor characteristics of an odorant which may be deficient in some regard, or supplement its existing odor impression to modify its quality, character or taste."

One or more of the norbornyl-substituted pyrans of this invention and conventional auxiliary perfume ingredients, for example, alcohols, aldehydes, ketones, nitriles, esters and essential oils, may be admixed so that the combined odors of the individual components produce a desired fragrance. Such perfume compositions are carefully balanced harmonious blends of essential oils, aroma chemicals, resinoids and other extracts of natural odorous materials. Each ingredient imparts its own characteristic effect in the composition. Thus, one or more of the norbornyl-substituted pyrans of this invention can be employed to impart novel characteristics into fragrance compositions.

Such compositions may contain up to about 80 weight percent of any one or more of the norbornyl-substituted pyrans of this invention. Ordinarily, at least about 0.001 weight percent of the norbornyl-substituted pyran is required to impart significant odor characteristics. Amounts in the range of from about 1 to 60 weight percent are preferred. The norbornyl-substituted pyrans of this invention may be formulated into concentrates containing from about 1 to about 60 weight percent of the chemical in an appropriate solvent. Such concentrates are then employed to formulate products such as colognes, soaps, etc., wherein the concentration of the chemical of this invention can be in the range of from about 0.001 to about 7 weight percent, depending upon the final product. For example, the concentration of the chemical of this invention will be of the order of about 0.001 to about 0.1 percent in detergents, and of the order of about 0.01 to about 7 weight percent in perfumes and colognes.

The norbornyl-substituted pyrans of this invention are useful as olfactory components of perfume compositions for detergents and soaps; space odorants and deodorants; perfumes; colognes; toilet water; bath preparations such as bath oils and bath solids; hair preparations such as lacquers, brilliantines, pomades and shampoos; cosmetic preparations such as creams, deodorants, hand lotions and sunscreens; powders such as talcs, dusting powders and face powders; and the like.

The following Examples are illustrative of the present invention.

EXAMPLE 1

Acrolein (376 g) dissolved in hexane (300 mL) was added with stirring to cyclopentadiene (468 g) in hexane (400 mL) during 1.1 h at 15°–43° C. After a further 1.6 h the reaction mixture was heated to reflux and water (8 mL) was removed via a Dean-and-Stark trap. After cooling (25°), 97% sulfuric acid (3 g) was added to the crude solution of bicyclo(2.2.1)hept-5-ene-3-carboxaldehyde. The mixture was heated at 76°–92° C. for 5.0 h, adding 2-methyl-1-penten-4-ol (896 g) during the first 1.0 h. Water (93 mL) was collected.

The reaction mixture was washed with saturated sodium bicarbonate solution (100 mL) and warm water (400 mL). Low boiling materials were evaporated (steam bath, water-ejector vacuum) and the residue was distilled to provide the desired product, $b_5 106°–109°$, 543 g.

GLC/MS, IR and 'H NMR data showed that the product consisted of a mixture of the desired norbornyl-substituted pyrans having the general structure:

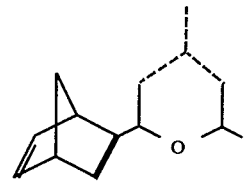

EXAMPLE 2

A solution of 3-methyl-5-norbornene-2-carboxaldehyde (55.4 g) and 2-methyl-1-penten-4-ol (60.3 g) was added during 1.7 h with stirring at 70°–77° C., to 97% sulfuric acid (0.15 g) in hexane (150 mL). Stirring was continued for an additional 4.0 h at 77°. Water was collected in a Dean-and-Stark trap.

The reaction product was worked up as described in Example 1 to provide the desired product, $b_2 96°–98°$, 41.4 g.

GLC/MS, IR and 'H NMR data showed that the product consisted of a mixture of the desired norbornyl-substituted pyrans having the general structure:

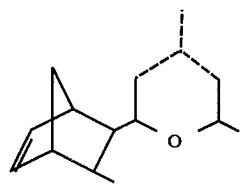

EXAMPLE 3

Employing procedures and materials similar to those described in Example 2, except that norbornane-2-carboxaldehyde was substituted for 3-methyl-5-norbornene-2-carboxaldehyde, there was produced a mixture of pyrans, $b_3 107°–109°$, having the general structure:

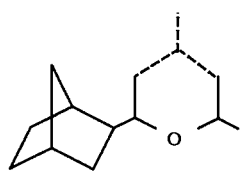

EXAMPLE 4

Employing the same procedures and materials as described in Example 2, except that 3-methylnorbornane-2-carboxaldehyde was the aldehyde used, there was produced a mixture of pyrans, $b_3$ 108°–110° C., having the general structure:

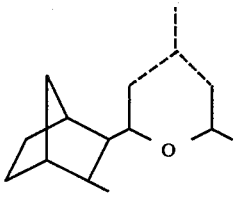

EXAMPLE 5

Employing procedures and materials similar to those described in Example 2, except that 2-methyl-1-buten-4-ol is substituted for 2-methyl-1-penten-4-ol, there can be produced a mixture of chemicals having the general structure:

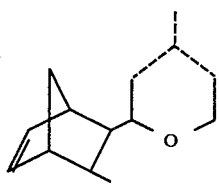

EXAMPLE 6

Viofleur Perfume Formulation

The norbornyl-substituted pyran mixture obtained according to Example 1 is incorporated into the violet type perfume formulation specified below:

| Ingredient | Parts By Weight |
|---|---|
| ALDEHYDE C-12 (L) 10 % SOL. ABSOLUTE VIOLET LEAVES F-46 IN D.E.P. ODORLESS | 10.0 |
| | 40.0 |
| VERTOFIX | 50.00 |
| THE NORBORNYL-SUBSTITUTED PYRAN PRODUCT OF EXAMPLE 1 | 50.0 |
| DUROFIX | 250.0 |
| NOVOVIOL ALPHA BETA | 600.00 |
| TOTAL | 1000.00 |

EXAMPLE 7

Petalia Perfume Formulation

The norbornyl-substituted pyran mixture obtained according to Example 1 is incorporated into the petal type perfume formulation specified below:

| Ingredient | Parts By Weight |
|---|---|
| GUAIACOL | 3.0 |
| ALDEHYDE C-14 FCC | 24.0 |
| BENZYL ACETATE FCC | 30.0 |
| PHENYL ACETALDEHYDE DMA FCC | 30.0 |
| BROMOSTYROL EXTRA | 30.0 |
| THE NORBORNYL-SUBSTITUTED PYRAN PRODUCT OF EXAMPLE 1 | 60.0 |
| DUROFIX | 223.0 |

-continued

| Ingredient | Parts By Weight |
|---|---|
| PHENYL ETHYL ALCOHOL FCC | 600.0 |
| TOTAL | 1000.0 |

EXAMPLE 8

Cucumber Perfume Formulation

The norbornyl-substituted pyran mixture obtained according to Example 2 is incorporated into the cucumber type perfume formulation specified below:

| Ingredient | Parts By Weight |
|---|---|
| OENANTHOL | 15.0 |
| BENZYL BENZOATE FCC | 25.0 |
| THE NORBORNYL-SUBSTITUTED PYRAN PRODUCT OF EXAMPLE 2 | 30.0 |
| METHYL OCTINE CARBONATE | 45.0 |
| ETHYL CAPRYLATE FCC | 60.0 |
| CYCLAMEN ALDEHYDE EXTRA FCC | 75.0 |
| OIL BERGAMOT RECTIFIED | 75.0 |
| LINALYL ACETATE SYNTHETIC FCC | 75.0 |
| OCTYL ACETATE FCC | 75.0 |
| PHENYL ETHYL ACETATE FCC | 225.0 |
| HYDROXY CITRONELLAL FCC | 300.0 |
| TOTAL | 1000.0 |

EXAMPLE 9

Mannequin Perfume Formulation

The norbornyl-substituted pyran mixture obtained according to Example 2 is incorporated into the mannequin type perfume formulation specified below:

| Ingredient | Parts By Weight |
|---|---|
| ALDEHYDE C-11 (LENIC) FCC | 1.4 |
| 10% SOL° ALDEHYDE C-12 FCC (MNA) IN D.E.P. ODORLESS | 3.5 |
| LINALOOL FCC SYNTHETIC | 3.5 |
| LINALYL ACETATE FCC SYNTHETIC | 3.5 |
| HEDIONE (FIRM.) | 3.5 |
| ISO BUTYL SALICYLATE FCC | 7.0 |
| TUBERIC ALCOHOL | 7.0 |
| 3% SOL. MUSQUIN IN ALCOHOL ETHYL FCC | 14.0 |
| COUMARIN | 14.0 |
| OIL GALBANUM | 14.0 |
| TINCTURE CIVET (D&O) | 14.0 |
| LEATHER COMPOUND | 17.5 |
| PHENYL ETHYL ALCOHOL FCC | 18.9 |
| STYROLYL ACETATE EXTRA | 21.0 |
| 10% SOL. CASTOREUM ABSOLUTE FB IN D.E.P. ODORLESS | 21.0 |
| 50% SOL. ABSOLUTE OAK MOSS DECOLORIZED IN D.E.P. ODORLESS | 21.0 |
| OIL LAVENDER FCC BARREME 38–42% | 24.5 |
| JASMIN COMPOUND | 24.5 |
| 10% SOL. OIL LABDANUM CISTUS DISTILLED IN D.E.P. ODORLESS | 28.0 |
| OIL PATCHOULY LIGHT COLOR | 28.0 |
| ANIMAL NOTE COMPOUND | 31.5 |
| 10% SOL. EXALTOLIDE 100% IN D.E.P. ODORLESS | 35.0 |
| HYDROXY CITRONELLAL FCC | 35.0 |
| METHYL IONONE GAMMA PURE | 49.0 |
| MUSK AMBRETTE | 49.0 |
| THE NORBORNYL-SUBSTITUTED PYRAN PRODUCT OF EXAMPLE 2 | 50.0 |
| CEDRENYL ACETATE | 63.7 |
| CEDRYL ACETATE | 66.5 |
| OIL BERGAMOT RECTIFIED | 330.5 |

| Ingredient | Parts By Weight |
|---|---|
| TOTAL | 1000.0 |

This invention has been described in terms of specific embodiments set forth in detail, but it should be understood that these are by way of illustration only and that the invention is not necessarily limited thereto. Other modifications and variations will be apparent from this disclosure and may be resorted to without departing from the spirit of this invention, as those skilled in the art will readily understand. Accordingly, such variations and modifications are considered to be within the scope of this invention and the following claims.

What is claimed is:

1. A norbornyl-substituted pyran of the formula:

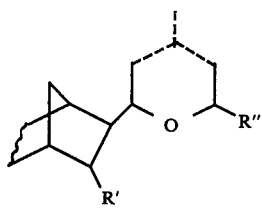

wherein the wavy line represents either a carbon-carbon single bond or a carbon-carbon double bond; and wherein the dashed lines represent either a carbon-carbon single bond or a carbon-carbon double bond such that two of the three dashed lines represent carbon-carbon single bonds; and wherein each R' and R", individually, is either hydrogen or a methyl group.

2. A norbornyl-substituted pyran according to claim 1 having the structure:

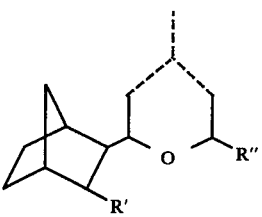

3. A norbornyl-substituted pyran according to claim 1 having the structure:

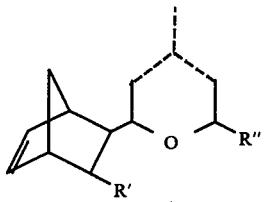

4. A norbornyl-substituted pyran according to claim 3 having the structure:

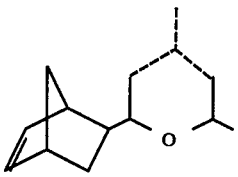

5. A norbornyl-substituted pyran according to claim 3 having the structure:

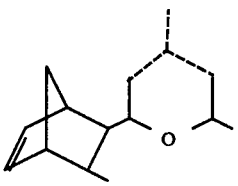

* * * * *

UNITED STATES PATENT AND TRADEMARK OFFICE
CERTIFICATE OF CORRECTION

PATENT NO. : 4,276,220
DATED : June 30, 1981
INVENTOR(S) : Brian J. Willis and John W. Dittrick It is certified that error appears in the above—identified patent and that said Letters Patent is hereby corrected as shown below:

Column 2, lines 47-48, "3-methyl-3-buten-1-01" should read
-- 3-methyl-3-buten-1-ol --.

Column 6, line 11, "2-methyl-1-penten-4-o1" should read
-- 2-methyl-1-penten-4-ol --.

Column 7, line 66, "Bromostyrol" should read --Bromstyrol--.

Signed and Sealed this

Fifteenth Day of September 1981

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,276,220

DATED : June 30, 1981

INVENTOR(S) : Brian J. Willis and John W. Dittrick

It is certified that error appears in the above—identified patent and that said Letters Patent is hereby corrected as shown below:

Column 2, lines 42-43, should read --wherein the dashed lines represent either a carbon-carbon single bond or a carbon-carbon double bond; and wherein the presence of three dashed lines--.

Column 2, line 48, "1-01" should read -- 1-ol --.

Column 3, line 14, "of" should read --or--.

Signed and Sealed this

First Day of December 1981

|SEAL|

Attest:

GERALD J. MOSSINGHOFF

Attesting Officer     Commissioner of Patents and Trademarks